United States Patent [19]
Hansen et al.

[11] Patent Number: 5,563,277
[45] Date of Patent: Oct. 8, 1996

[54] PROCESS FOR PREPARING BENZYL-SUBSTITUTED RHODANINE DERIVATIVES

[75] Inventors: Marvin M. Hansen; Allen R. Harkness; Michael J. Martinelli, all of Indianapolis; Vien V. Khau, Carmel, all of Ind.

[73] Assignee: Eli Lilly and Company, Indianapolis, Ind.

[21] Appl. No.: 361,281

[22] Filed: Dec. 21, 1994

[51] Int. Cl.$^6$ .................................................. C07D 277/04
[52] U.S. Cl. ........................... 548/182; 548/186; 548/189
[58] Field of Search ...................... 548/182, 186, 548/189

[56] References Cited

U.S. PATENT DOCUMENTS 5,216,002  6/1993  Gidda et al. ............................ 514/369

FOREIGN PATENT DOCUMENTS 343643  11/1989  European Pat. Off. ........ A61K 31/41
391644  10/1990  European Pat. Off. ........ C07D 277/14

OTHER PUBLICATIONS

Polniaszek, et al., J. Org. Chem., 55, 215, (1990).
Ibuka, et al., Chem. Pharm. Bull., 23(11), 2779, (1975).
Phillips, et al., J. Org. Chem., 57, 4047 (1992).
Field, J. Org. Chem., 43, 1084 (1978).
Evans, et al., Tetrahedron Letters, 26, 3783 (1985).
Singh, et al., Chem. Rev., 81, 175 (1981).
Hoff, et al., Tetrahedron Letters, 51, 5199 (1972).
Yasuda, et al., Chem. Pharm. Bull., 37, 1682 (1989).
Annunziata, et al., J. Chem. Soc., Chem. Commun., 1138 (1983).
Tanabe et al., Tetrahedron Letters, 32, 383 (1991).
Schmolka et al., J. ACS, 79, 4716 (1957).

*Primary Examiner*—Johann Richter
*Assistant Examiner*—Laura R. Cross
*Attorney, Agent, or Firm*—Joseph A. Jones; Roger S. Benjamin; Douglas J. Taylor

[57] ABSTRACT

The instant invention provides a novel process for preparing benzyl-substituted rhodanine derivatives. The process is particularly useful for synthesizing the enantiomers of such derivatives. Also provided are novel benzyl-substituted mercaptopropanoic acids and benzyl-substituted thiazolidinones. Such compounds are useful for treating inflammatory bowel disease and, accordingly, the present invention provides a method of treating inflammatory bowel disease in mammals utilizing such novel compounds as well as pharmaceutical compositions containing same.

33 Claims, No Drawings

PROCESS FOR PREPARING BENZYL-SUBSTITUTED RHODANINE DERIVATIVES

BACKGROUND OF THE INVENTION

Benzyl substituted rhodanine derivatives of the general formula

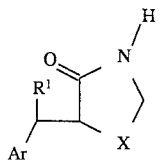

wherein $R^1$, and X are as set forth below, are known to be active in treating inflammation, inflammatory bowel disease (hereinafter IBD), allergies, arthritis, hypoglycemia and muscular dystrophy and in preventing ischemia induced cell damage. For example, U.S. Pat. No. 5,216,002 discloses that certain benzyl-substituted rhodanine derivatives are useful for treating IBD. EPO Publication No. 391644, on the other hand, discloses the effectiveness of such compounds for treating inflammation, arthritis, and muscular dystrophy and for preventing ischemia induced cell damage. EPO Publication No. 343643 describes the use of such compounds for treating allergies and inflammation, while EPO Publication No. 587377 discloses these compounds as being effective in treating hypoglycemia.

All of the above patents and publications describe various processes for making the benzyl-substituted rhodanine derivatives disclosed therein. U.S. Pat. No. 5,216,002, further, describes a process for selectively isolating by kinetic resolution, in substantially pure enantiomeric form, one of the enantiomers of a racemic mixture of a benzyl-substituted rhodanine. The process disclosed therein comprises oxidizing the racemic sulfide compound until the undesired enantiomer of the sulfide substrate has been converted to its sulfoxide analog and then separating the unreacted portion of the sulfide substrate from the reaction mixture.

The current processes for preparing benzyl-substituted rhodanine derivatives, as set forth above, are, in general, satisfactory. However, there is room for improvement in process yield and the product purity obtained therefrom, particularly for compounds which have a stereocenter at the 5-position of the rhodanine ring. The current process for preparing compounds having such stereocenter (as set forth in U.S. Pat. No. 5,216,002) sets the center in the last step of the process which results in a low overall yield of desired product because a substantial amount of the undesired enantiomer must be discarded. Furthermore, the chromatographic purification step required to recover the desired enantiomer is difficult to perform, especially on a production scale. Finally, the process is expensive requiring large amounts of catalyst.

The present invention provides an improved process for preparing benzyl-substituted rhodanine derivatives. The process of the present invention is particularly useful for synthesizing the enantiomers of such derivatives since the chiral center is set at an early stage of the synthesis resulting in a higher overall yield of the desired enantiomer. In addition, the process can be performed with inexpensive, readily available reagents. Other objects, features and advantages of the present invention will become apparent from the subsequent description and the appended claims.

SUMMARY OF THE INVENTION

The present invention provides a process for preparing a compound of the Formula I

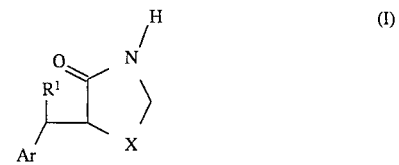

wherein:

Ar is (i) phenyl, (ii) phenyl substituted with from one to three substituents independently selected from $C_1$–$C_8$ alkyl, $C_2$–$C_6$ alkenyl, $C_2$–$C_6$ alkynyl, $C_1$–$C_8$ alkoxy, $C_1$–$C_8$ alkylthio, trifluoromethyl, $C_1$–$C_4$ alkylphenyl, phenyl, F, Cl, hydroxy, phenoxy, $C_1$–$C_4$ alkyloxyphenyl, thiophenyl, $C_1$–$C_4$ alkylthiophenyl, —$N(R^6)_2$ or —$N(R^6)SO_2R^6$, where each $R^6$ is independently hydrogen or $C_1$–$C_6$ alkyl or (iii) 1- or 2-napthyl;

$R^1$ is $C_1$–$C_6$ alkyl, $C_1$–$C_4$ alkylphenyl, hydrogen, phenyl or phenyl substituted with one or two substituents independently selected from Cl, F, $C_1$–$C_4$ alkyl, $C_1$–$C_4$ alkoxy, trifluoromethyl, $NH_2$, —$NH(C_1$–$C_4$ alkyl), —$N(C_1$–$C_4$ alkyl)$_2$ or $C_1$–$C_4$ alkylthio; and X is S=(O)$_m$ where m is 0, 1 or 2, comprising reducing a thiazolidinone of the Formula II.

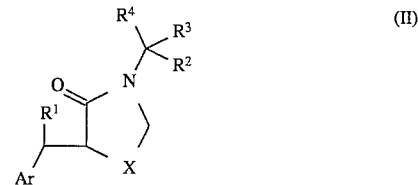

wherein:

Ar, $R^1$, and X are as defined above; and $R^2$ and $R^3$ are each independently hydrogen, $C_1$–$C_6$ alkyl, phenyl, phenyl substituted with from one to three substituents independently selected from $C_1$–$C_6$ alkyl or —$CO_2R^5$, where $R^5$ is hydrogen or $C_1$–$C_6$ alkyl; and $R^4$ is phenyl or phenyl substituted with from one to three substituents independently selected from $C_1$–$C_6$ alkyl, or —$CO_2R^5$, where $R^5$ is hydrogen or $C_1$–$C_6$ alkyl; with an alkali or alkali-earth metal in the presence of ammonia or an amine of the formula $H_2NR^7$ where $R^7$ is $C_1$–$C_6$ alkyl.

Compounds of Formula II are novel. As such, the instant invention provides such compounds, and the pharmaceutically acceptable salts thereof, as well.

The present invention, further, provides new compounds of the Formula III

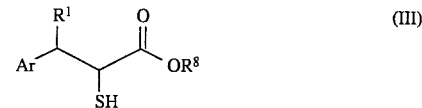

wherein:

Ar is (i) phenyl, (ii) phenyl substituted with from one to three substituents independently selected from $C_1$–$C_8$ alkyl, $C_2$–$C_6$ alkenyl, $C_2$–$C_6$ alkynyl, $C_1$–$C_8$ alkoxy, $C_1$–$C_8$ alkylthio, trifluoromethyl, $C_1$–$C_4$ alkylphenyl, phenyl, F, $C_1$, hydroxy, phenoxy, $C_1$–$C_4$ alkyloxyphenyl, thiophenyl, $C_1$–$C_4$ alkylthiophenyl, —$N(R^6)_2$ or —$N(R^6)SO_2R^6$, where each $R^6$ is independently hydrogen or $C_1$–$C_6$ alkyl, or (iii) 1- or 2-napthyl;

$R^1$ is $C_1$–$C_6$ alkyl, $C_1$–$C_4$ alkylphenyl, hydrogen, phenyl or phenyl substituted with one or two substituents independently selected from Cl, F, $C_1$–$C_4$ alkyl, $C_1$–$C_4$ alkoxy, trifluoromethyl, $NH_2$, $-NH(C_1-C_4$ alkyl), $-N(C_1-C_4$ alkyl)$_2$ or $C_1-C_4$ alkylthio; and $R^8$ is hydrogen, or $C_1-C_6$ alkyl; or a pharmaceutically acceptable salt thereof. Such compounds are useful as intermediates for preparing the compounds of Formula II.

The compounds of Formulae II and III, while useful as intermediates in preparing the compounds of Formula I, are also useful in treating inflammatory bowel disease in a mammal suffering from or susceptible to such disease. As such, the present invention, further, provides a method of treating inflammatory bowel disease comprising administering to a mammal in need of such treatment a therapeutically effective amount of a compound of Formulae II or III.

Since the compounds of Formulae II and III possess pharmacological activity, a final aspect of the present invention provides pharmaceutical compositions comprising as active ingredient a compound of Formulae II or III, or a pharmaceutically acceptable salt thereof, in association with one or more pharmaceutically acceptable diluents, carriers or excipients therefor.

DETAILED DESCRIPTION OF THE INVENTION

As used herein, the term "$C_1-C_8$ alkyl" refers to straight and branched chain aliphatic alkyl groups of 1 to 8 carbon atoms. Typical $C_1-C_8$ alkyl groups include methyl, ethyl, propyl, isopropyl, butyl, isobutyl, sec-butyl, tertbutyl, n-pentane, isopentane, n-hexane, isohexane and the like. The term "$C_1-C_8$ alkyl" includes within its definition the terms "$C_1-C_4$ alkyl" and "$C_1-C_6$ alkyl".

The term "$C_1-C_8$ alkoxy" represents a straight or branched alkyl chain having 1 to 8 carbon atoms which chain is attached to the remainder of the molecule by an oxygen atom. Typical $C_1-C_8$ alkoxy groups include methoxy, ethoxy, propoxy, isopropoxy, butoxy, isobutoxy, sec-butoxy, tert-butoxy, pentoxy, hexoxy and the like. The term "$C_1-C_8$ alkoxy" includes within its definition "$C_1-C_4$ alkoxy".

The term "$C_2-C_6$ alkenyl" refers to straight and branched chains of 2 to 6 carbon atoms, both inclusive, having a double bond. As such, the term includes ethylene, propylene, isopropylene, 1-butene, 2-butene, 2-methyl-1-propene, 1-pentene, 2-pentene, 2-methyl-2-butene and the like.

The term "$C_2-C_6$ alkynyl" refers to straight and branched chain radicals of 2 to 6 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne and the like.

The term "$C_1-C_8$ alkylthio" represents a straight or branched alkyl chain having one to eight carbon atoms, which chain is attached to the remainder of the molecule by a sulfur atom. Typical $C_1-C_8$ alkylthio groups include methylthio, ethylthio, n-propylthio, isopropylthio, n-butylthio, t-butylthio and the like. The term "$C_1-C_8$ alkylthio" includes within its definition "$C_1-C_4$ alkylthio".

"$C_1-C_4$ alkylphenyl" represents a straight or branched chain alkyl group having from one to four carbon atoms attached to a phenyl ring. Typical $C_1-C_4$ alkylphenyl groups include methylphenyl, ethylphenyl, n-propylphenyl, isopropylphenyl, n-butylphenyl, isobutylphenyl, and tert-butylphenyl.

The term "$C_1-C_4$ alkylthiophenyl" represents a straight or branched chain alkyl group having from one to four carbon atoms attached to a thiophenyl moiety. Typical $C_1-C_4$ alkylthiophenyl groups include methylthiophenyl ethylthiophenyl, isobutylthiophenyl and the like.

In similar fashion, the term "$C_1-C_4$ alkyloxyphenyl" represents a straight or branched chain alkyl group having from one to four carbon atoms attached to phenoxy moiety. Typical $C_1-C_4$ alkyloxyphenyl groups include methyloxyphenyl, ethyloxyphenyl, propyloxyphenyl and the like.

A preferred group of compounds of Formula I which can be prepared by the process of the instant invention are those having a substituent pattern independently selected from among the following (a) Ar is phenyl substituted with from one to three substituents independently selected from $C_1-C_8$ alkyl, $C_1-C_8$ alkoxy, $C_1-C_4$ alkylphenyl, phenyl, F, Cl, hydroxy, phenoxy, $C_1-C_4$ alkylthiophenyl, or $-N(R^6)SO_2R^6$ where each $R^6$ is independently hydrogen or $C_1-C_6$ alkyl; (b) $R^1$ is hydrogen; and (c) X is $S=(O)_m$ where m is 0.

Of this preferred group of compounds somewhat more preferred compounds of Formula I which can be prepared according to the process of the present invention are those compounds wherein Ar is phenyl substituted with from one to three substituents independently selected from $C_1-C_4$ alkyl, $C_1-C_6$ alkoxy or hydroxy. Even more preferred compounds of Formula I which can be prepared according to the instantly claimed process are those wherein Ar is phenyl substituted with hydroxy at the 4-position and a $C_1-C_4$ alkyl group at the 3- and 5-positions.

The most preferred compounds which can be prepared by the instant process are (R)-(+)-[[3,5-bis(1,1-dimethylethyl)-4-hydroxyphenyl]methyl]-4-thiazolidinone and (S)-(–)-[[3,5-bis (1,1-dimethylethyl)-4-hydroxyphenyl]methyl]-4-thiazolidinone.

Compounds of Formula II wherein Ar is phenyl substituted with from one to three substituents independently selected from $C_1-C_8$ alkyl, $C_1-C_8$ alkoxy, $C_1-C_4$ alkylphenyl, phenyl, F, Cl, hydroxy, phenoxy, $C_1-C_4$ alkylthiophenyl, or $-N(R^6)SO_2R^6$ where each $R^6$ is independently hydrogen or $C_1-C_6$ alkyl; $R^1$ is hydrogen; X is $S=(O)_m$ where m is 0; $R^2$ and $R^3$ are each independently hydrogen, $C_1-C_4$ alkyl, phenyl or phenyl substituted with $-CO_2(C_1-C_4$ alkyl); and $R^4$ is phenyl or phenyl substituted with $CO_2(C_1-C_4$ alkyl) are preferred for use in the method of treating inflammatory bowel disease of the present invention. Such compounds are also preferred substrates in the process for preparing compounds of Formula I instantly claimed.

Of this preferred group of compounds of Formula II somewhat more preferred are those compounds wherein Ar is phenyl substituted with from one to three substitutents independently selected from $C_1-C_4$ alkyl, $C_1-C_6$ alkoxy or hydroxy.

Even more preferred are those compounds of Formula II wherein Ar is phenyl substituted with hydroxy at the 4-position and a $C_1-C_4$ alkyl group at the 3- and 5-positions.

The most preferred compound of Formula II is 5-[[3,5-bis( 1,1-dimethylethyl)-4-hydroxyphenyl]methyl]-3-(1 -phenylethyl)-4-thiazolidinone.

Compounds of Formula III which are preferred according to the present invention include those compounds wherein Ar is phenyl substituted with from one to three substitutents independently selected from $C_1-C_8$ alkyl, $C_1-C_8$ alkoxy, $C_1-C_4$ alkylphenyl, phenyl, F, Cl, hydroxy, phenoxy, $C_1-C_4$ alkylthiophenyl, or $-N(R^6)SO_2R^6$ where each $R^6$ is independently hydrogen or $C_1-C_6$ alkyl and $R^1$ and $R^8$ are each hydrogen.

Of this preferred group of compounds of Formula III somewhat more preferred are those compounds wherein Ar is phenyl substituted with from one to three substituents independently selected from $C_1$–$C_4$ alkyl, $C_1$–$C_6$ alkoxy or hydroxy.

Even more preferred are those compounds of Formula III wherein Ar is phenyl substituted with hydroxy at the 4-position and a $C_1$–$C_4$ alkyl group at the 3- and 5-positions.

The most preferred compound of Formula III provided by the present invention is 3-[3,5-bis(1,1-dimethylethyl)-4-hydroxyphenyl]-2-mercaptopropanoic acid.

Pharmaceutically acceptable salts are considered to be encompassed within the compounds and method of the present invention. The term "pharmaceutically acceptable salts" refers to salts of the compounds of Formulae II or III which are substantially non-toxic to living organisms.

Typical pharmaceutically acceptable salts include those salts prepared by reactions of the compounds of Formulae II or III with a pharmaceutically acceptable mineral or organic acid, or a pharmaceutically acceptable alkali metal or organic base depending on the types of substituents present on the compounds of the Formulae.

Examples of pharmaceutically acceptable mineral acids which may be used to prepare pharmaceutically acceptable salts include hydrochloric acid, sulfuric acid, hydrobromic acid, hydroiodic acid, phosphoric acid and the like. Examples of pharmaceutically acceptable organic acids which may be used to prepare pharmaceutically acceptable salts include aliphatic mono and dicarboxylic acids, oxalic acid, carbonic acid, citric acid, succinic acid, phenyl-substituted alkanoic acids, aliphatic and aromatic sulfonic acids and the like. Such pharmaceutically acceptable salts prepared from mineral or organic acids thus include hydrochloride, hydrobromide, nitrate, sulfate, pyrosulfate, bisulfate, sulfite, bisulfite, phosphate, monohydrogen phosphate, dihydrogen phosphate, metaphosphate, pyrophosphate, hydroiodide, hydrofluoride, acetate, propionate, formate, oxalate, citrate, lactate, p-toluene sulfonate, methane sulfonate, maleate and the like.

It should be recognized that any particular anion or cation forming a part of any salt of this invention is not critical, so long as the salt, as a whole, is pharmacologically acceptable and as long as the anion or cation moiety does not contribute undesired qualities.

Many compounds of Formulae II or III which contain a hydroxy or sulfoxide group may be converted to a pharmaceutically acceptable salt by reaction with a pharmaceutically acceptable alkali metal or organic base. Examples of pharmaceutically acceptable organic bases which may be used to prepare pharmaceutically acceptable salts include ammonia, amines such as triethanolamine, triethylamine, ethylamine, and the like. Examples of pharmaceutically acceptable alkali metal bases include compounds of the general formula $MOR^9$, where M represents an alkali metal atom, e.g. sodium, potassium, or lithium, and $R^9$ represents hydrogen or $C_1$–$C_6$ alkyl.

The compounds of Formulae II and III have a chiral center and, as such, can exist either as individual stereoisomers or in racemic form. The compounds, formulations and method of the present invention encompass such stereoisomers as well as the racemates. The stereoisomers of the compounds of Formulae II and III may be obtained according to procedures well known in the art. The compounds of Formulae II and III (whether as stereoisomers or as the racemate) are prepared according to the following general procedure:

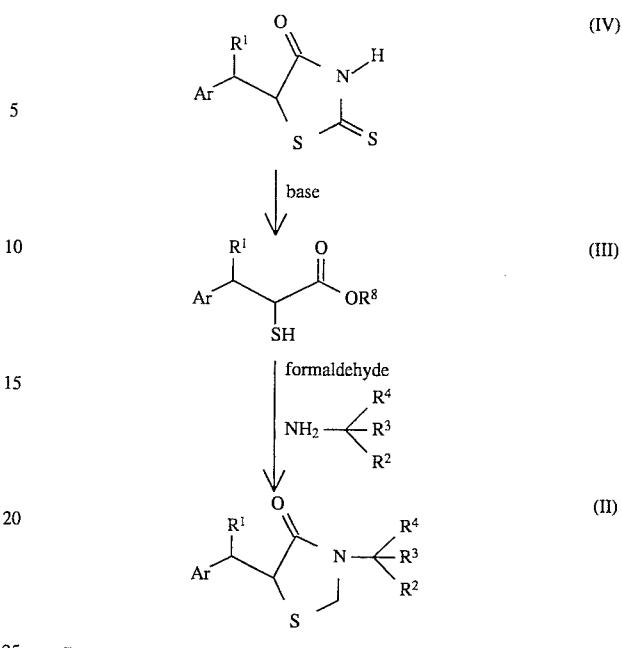

In the above procedure, a benzyl substituted rhodanine derivative of Formula IV is hydrolyzed using an aqueous base of the formula $MOR^8$ where M and $R^8$ are as previously defined or a $C_1$–$C_6$ alkoxide in a $C_1$–$C_6$ alcohol or polar solvent, such as dimethylformamide or dimethylsulfoxide to provide a thiol acid or thiol acid ester of Formula III. Such thiol acid or thiol acid ester is then readily converted to a benzyl substituted rhodanine derivative of Formula II via reaction with formaldehyde, and an amine of the formula

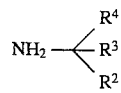

where $R^2$, $R^3$ and $R^4$ are also as previously defined.

The reaction scheme detailed above provides compounds of Formula II wherein X is —S— (i.e. m is 0). Compounds of Formula II wherein X is —SO— or —$SO_2$— (i.e., wherein m is 1 or 2, respectively) are readily prepared from the sulfide (m=0) by treatment with an oxidizing agent, such as m-chloroperbenzoic acid, in an appropriate organic solvent, such as chloroform, for a time sufficient to effect the desired oxidation.

The compounds of Formula II, in addition to being useful for treating inflammatory bowel disease, are also useful for preparing compounds of Formula I. Such compounds of Formula I are known to be useful for treating a variety of ailments (see, e.g., U.S. Pat. No. 5,216,002 and European Patent Application Nos. 391644, 343643 and 587377). As such, the present invention also provides a process for preparing compounds of Formula I comprising reducing a thiazolidinone of the Formula II with an alkali or alkali earth metal in the presence of ammonia or an amine of the formula $H_2NR^7$ where $R^7$ is $C_1$–$C_6$ alkyl.

According to the process of the present invention a thiazolidinone compound of Formula II is dissolved in a solvent mixture consisting of ammonia or a low molecular weight amine [i.e., an amine of the formula $H_2N(C_1$–$C_6$ alkyl)] and an ethereal or aromatic co-solvent. Ammonia is preferred in the instantly claimed process. Certain of the thiazolidinone substrates employed in the process of the present invention are soluble in just ammonia or the low molecular weight amine solvent, while others are not. For those substrates which are not soluble in just ammonia or the low molecular weight amine, an ethereal or aromatic co-solvent is required. Suitable ethereal co-solvents include tetrahydrofuran, diethyl ether, dimethoxyethane, diethoxyethane, tert-butyl methyl ether, glymes and the like. Suitable aromatic co-solvents include toluene, benzene, xylene, cumene and the like. While the ratio of ammonia/amine to ethereal/aromatic co-solvent is not critical, a preferred ratio of such substances is from 1 part ammonia/amine to 1 part co-solvent to 1 part ammonia/amine to 4 parts co-solvent. The most preferred ratio is 1 part ammonia/amine to 2 parts co-solvent. If larger amounts of co-solvent are employed, the desired reaction will still proceed but at a slower rate than if a ratio in the preferred ratio range is employed. In addition, the amount of solvent used should be sufficient to ensure that all compounds stay in solution until the desired reaction is complete.

After the compound of Formula II has been dissolved, an alkali or alkali earth metal is then added to the reaction mixture. Acceptable alkali earth metals include lithium, sodium, potassium and the like. Acceptable alkali earth metals include calcium, magnesium and the like. The most preferred metal is lithium. In general, excess amounts of the alkali or alkali earth metal should be avoided as this leads to overreduction of the thiazolidinone substrate. For best results, approximately two moles of alkali metal should be utilized for every mole of thiazolidinone substrate. However, only one mole of alkali earth metal need be utilized for every mole of thiazolidinone substrate.

The process of the present invention can be conducted at any temperature which is between the freezing and boiling points of the particular solvent mixture employed. Furthermore, if a pressure reactor is employed, reaction temperatures above the atmospheric pressure boiling point of the solvent mixture may be employed as well.

The process of the present invention is then conducted until substantially all of the thiazolidinone substrate has been reduced. Standard analytical techniques, such as HPLC, can be used to monitor the reaction in order to determine when substrate reduction is complete. Once complete, the reaction is quenched to prevent overreduction and the desired product is then obtained using techniques well known to those skilled in the art.

Compounds of Formula II wherein Ar is phenyl substituted with hydroxy at the 4-position have an internal proton which protonates the ethylbenzene anion formed during formation of the compounds of Formula I. If the compound of the Formula II does not have an internal proton, a proton source may be added to facilitate the reaction. Preferred proton sources include $C_1$–$C_6$ alcohols or phenol. The preferred proton source is tert-butyl alcohol.

Stereoisomers of compounds of Formula I are known. However the known process for preparing such stereoisomers has a low overall yield of desired enantiomer, requires large amounts of an expensive catalyst and employs a chromatographic purification step which is difficult to perform on a production scale process. The process of the present invention provides an improved method for synthesizing the enantiomers of the compounds of Formula I. By setting the chiral center at an early stage in the synthesis, higher overall yields of the desired enantiomer are obtained. Such chiral center can be set by using a chiral amine reagent when cyclizing a compound of Formula III to a compound of Formula II, thereby providing an efficient method for resolving the thiol acid and assembling the triazolidinone ring in one step. Preferred chiral amines are the enantiomers of 2-methylbenzylamine; namely, (R)-2-methylbenzylamine and (S)-2-methylbenzylamine.

The rhodanine derivatives of Formula IV are either known in the art or can be readily prepared from commercially available aldehydes and rhodanines using conventional techniques. All other reactants used to prepare the compounds of Formulas II and III are commercially available, as are all reagents employed in the process of the present invention.

The following examples further illustrate the preparation of the compounds of this invention as well as the compounds used in the method of this invention. The examples also illustrate the process of the present invention. The examples are illustrative only and are not intended to limit the scope of the invention in any way.

EXAMPLE 1

(S)-5-[[3,5-bis (1,1-dimethylethyl)-4-hydroxyphenyl]methyl]-4-thiazolidinone

A. Preparation of 3-[3,5-bis(1,1-dimethylethyl)-4-hydroxyphenyl]-2-mercaptopropanoic acid To 114.5 g of 5-[[3,5-bis(1,1-dimethylethyl)-4-hydroxyphenyl]methyl]-2-thioxo-4-thiazolidinone, 815 ml of 2M sodium hydroxide was added. The resultant mixture was heated to reflux temperature over the course of one hour and maintained at reflux for 2 hours. The mixture was cooled in an ice/water bath to 15° C. and 290 ml of 6M hydrochloric acid was added dropwise under a nitrogen atmosphere over 15 minutes, keeping the temperature of the mixture below 16° C. The resultant solid was dissolved by adding 600 ml of ethyl acetate to the mixture. The organic layer was separated, washed 3 times with 100 ml of saturated sodium chloride solution, dried over sodium sulfate and then the solvent was removed in vacuo to yield 100.3 g (100% of yield) of the subtitled intermediate. mp 137°–140° C.

Analysis Calculated for $C_{17}H_{26}O_3S$: Theory: C, 65.77; H, 8.44; Found: C, 66.03; H, 8.49.

B. Preparation of (3αR, 5S)-5-[[3,5-bis (1,1-dimethylethyl)-4-hydroxyphenyl]methyl]-3-(1-phenyl ethyl)-4-thiazolidinone Under a nitrogen atmosphere and using a mechanical stirrer, 149 g of 3-[3,5-bis-(1,1 dimethylethyl)-4-hydroxyphenyl]-2-mercaptopropanoic acid (prepared substantially in accordance with the method described above) and 14.4 g of paraformaldehyde were added to 1 liter of toluene. (R)-2-methylbenzylamine (62 ml) was added and the mixture was heated to reflux temperature for one hour with removal of water by means of a Dean-Stark apparatus. The resultant yellow homogeneous solution was allowed to cool to room temperature and washed with 400 ml of a 0.5M hydrochloric acid solution, 250 ml of a saturated sodium bicarbonate solution and 200 ml of a saturated sodium chloride solution. The cloudy organic layer was dried with sodium sulfate, passed through 100 g of 230–400 mesh silica gel and then concentrated in vacuo to yield 207 g of a cloudy oil. Using a mechanical stirrer, the oil was dissolved in 1.5 liter of hexanes and heated to reflux temperature then allowed to cool to room temperature overnight. The resultant precipitate was isolated, filtered and rinsed with hexanes then dried in vacuo at 45° C. to obtain 77.1 g (38% yield) of subtitled compound as a white, sandy solid. mp 125°–126° C.

$[\alpha]589=+4.3(c=1,CHCl_3)$

Analysis Calculated for $C_{26}H_{35}NO_2S$: Theory: C, 73.37; H, 8.29; N, 3.29; Found: C, 73.50; H, 8.29; N, 3.28.

C. Preparation of (S)-5-[[3,5-bis(1,1-dimethylethyl)-4-hydroxyphenyl]methyl]-4-thiazolidinone Under a nitrogen atmosphere and using a mechanical stirrer, 100 ml of ammonia was condensed at −78° C. into a flask to which was added 25 g of the compound of Example 1B, above, dissolved in 100 ml of dry tetrahydrofuran. An additional 150 ml of tetrahydrofuran was then added to the reaction mixture to dissolve all of the solids. Lithium wire (0.83 g; 118 mmoles; 2.0 equiv) was added to the reaction mixture in approximately 0.02–0.04 gram pieces over a period of 20 minutes. Ten minutes after the last piece of lithium was added, the light green reaction solution was quenched with 17 g of ammonium chloride, the cooling bath was removed and ammonia was allowed to evolve for 45 minutes. After ammonia evolution was completed, the reaction mixture was partitioned between 250 ml of ethyl acetate and 250 ml of water. The organic layer was separated and washed with 100 ml of a 1M hydrochloric acid solution then with a solution of 150 ml of water and 20 ml of brine, and, finally, with 50 ml of brine. The organic layer was then dried over sodium sulfate and evaporated to yield 22.3 g of a white foam. This foam was purified by silica gel chromatography using 5 liters of 3:2 hexanes/ethyl acetate then evaporated to afford 13.7 g of a white solid. The solid was dissolved in 95 ml of 3:1 hexanes/ethyl acetate and the resulting solution was heated to reflux temperature. Solids crystallized upon cooling to room temperature overnight. The resulting slurry was cooled in an ice/water bath for 30 minutes and then filtered. The recovered crystals were rinsed with about 20 ml of hexanes and dried in vacuo at 45° C. for 4 hours to yield 10.8 g of title product (57% yield). mp 149°–150° C.

[α]589=−79.3 (c=1, CHCl$_3$)

Analysis Calculated for C$_{18}$H$_{27}$NO$_2$S: Theory: C, 67.25; H, 8.47; N, 4.36; S, 9.97; Found: C, 67.50; H, 8.33; N, 4.58; S, 9.99.

EXAMPLE 2

(R)-5-[[3,5-bis(1,1-dimethylethyl)-4-hydroxyphenyl]methyl]-4-thiazolidinone

A. Preparation of (3αS, 5R)-5-[[3,5-bis(1,1-dimethylethyl)- 4-hydroxyphenylmethyl]-3-(1-phenylethyl)-4-thiazolidinone The subtitled compound was prepared substantially in accordance with the procedure set forth in Examples 1A and 1B with the major exception being that (S)-2-methylbenzylamine was employed in place of (R)-2-methylbenzylamine. Such process provided 15 g of subtitled compound (36% yield). mp 125°–126° C.

[α]589=−5.2 (c=1, CHCl$_3$)

Analysis Calculated for C$_{26}$H$_{35}$NO$_2$S: Theory: C, 73.37; H, 8.29; N, 3.29; Found: C, 73.13; H, 8.21; N, 3.46.

B. Preparation of (R)-5-[[3,5-bis(1,1-dimethylethyl)-4-hydroxyphenyl]methyl]-4-thiazolidinone The title compound was prepared, substantially, in accordance with the process in Example 1C to provide 11.9 of title compound (57% yield). mp 149°–150° C.

[α]589=+79.5 (c=1, CHCl$_3$)

Analysis Calculated for C$_{18}$H$_{27}$NO$_2$S: Theory: C, 67.25; H, 8.47; N, 4.36; Found: C, 67.64; H, 8.20; N, 4.59.

EXAMPLE 3

(R)-(+)-5-[[3,5-bis(1,1-dimethylethyl)-4-hydroxyphenyl]methyl]-4-thiazolidinone

The title compound was prepared using 6.9 mmoles (0.58 equivalents) of lithium following the procedure of Example 1. HPLC assay of the reaction solution after lithium addition was completed indicated the title compound had been obtained in 19% non-isolated yield.

EXAMPLE 4

(R)-(+)-5-[[3,5-bis (1,1-dimethylethyl)-4-hydroxyphenyl]methyl]-4-thiazolidinone The title compound was prepared using 62.4 mmoles (5.25 equivalents) of lithium following the procedure of Example 1. HPLC assay of the reaction solution after lithium addition was completed indicated the title compound had been obtained in 11% non-isolated yield.

EXAMPLE 5

(R)-(+)-5-[[3,5-bis (1,1-dimethylethyl)-4-hydroxyphenyl]methyl]-4-thiazolidinone The title compound was prepared from 2.016 g (4.74 mmoles) of (3αS,5R)-5-[[3,5-(1,1-dimethylethyl)-4-hydroxyphenyl]methyl]-3-(1-phenylethyl)-4-thiazolidinone using 1.90 mmoles (0.4 equivalents) of sodium following the procedure of Example 1C. HPLC assay of the reaction solution after sodium addition was completed indicated the title compound had been obtained in 10.7% non-isolated yield.

EXAMPLE 6

(R)-(+)-5-[[3,5-bis (1,1-dimethylethyl)-4-hydroxyphenyl]methyl]-4-thiazolidinone The title compound was prepared from 2.80 g (6.59 mmoles) of (3αS,5R)-5-[[3,5-(1,1-dimethylethyl)-4-hydroxyphenyl]methyl]-3-(1-phenylethyl)-4-thiazolidinone using 6.74 mmoles (1 equivalent) of sodium following the procedure of Example 1C. HPLC assay of the reaction solution after sodium addition was completed indicated the title compound had been obtained in 31.2% non-isolated yield.

EXAMPLE 7

(R)-(+)-5-[[3,5-bis(1,1-dimethylethyl)-4-hydroxyphenyl]methyl]-4-thiazolidinone

The title compound was prepared from 2.016 g (4.74 mmoles) of (3αS,5R)-5-[[3,5-(1,1-dimethylethyl)-4-hydroxyphenyl]methyl]-3-(1-phenylethyl)-4-thiazolidinone using 9.48 mmoles (2 equivalents) of sodium following the procedure of Example 1C. HPLC assay of the reaction solution after sodium addition was completed indicated the title compound had been obtained in 59.2% non-isolated yield.

EXAMPLE 8

(R)-(+)-5-[[3,5-bis (1,1-dimethylethyl)-4-hydroxyphenyl]methyl]-4-thiazolidinone The title compound was prepared from 2.016 g (4.74 mmoles) of (3αS,5R)-5-[[3,5-(1,1-dimethylethyl)-4-hydroxyphenyl]methyl]-3-(1-phenylethyl)-4-thiazolidinone using 13.32 moles (2.81 equivalents) of sodium following the procedure of Example 1C. HPLC assay of the reaction solution after sodium addition was completed indicated the title compound had been obtained in 77.3% non-isolated yield.

EXAMPLE 9

(R)-(+)-5-[[3,5-bis(1,1-dimethylethyl)-4-hydroxyphenyl]methyl]-4-thiazolidinone

The title compound was prepared from 2.07 g (4.86 mmoles) of (3αS,5R)-5-[[3,5-(1,1-dimethylethyl)-4-hydroxyphenyl]methyl]-3-(1-phenylethyl)-4-thiazolidinone using 1.035 mmoles (0.5 equivalents) of calcium following the procedure of Example 1C. HPLC assay of the reaction solution after calcium addition was completed indicated the title compound had been obtained in 12.1% non-isolated yield.

EXAMPLE 10

(R)-(+)-5-[[3,5-bis(1,1-dimethylethyl)-4-hydroxyphenyl]methyl]-4-thiazolidinone

The title compound was prepared from 2.07 g (4.86 mmoles) of (3αS,5R)-5-[[3,5-(1,1-dimethylethyl)-4-hydroxyphenyl]methyl]-3-(1-phenylethyl)-4-thiazolidinone using 4.86 mmoles (1 equivalent) of calcium following the procedure of Example 1C. HPLC assay of the reaction solution after calcium addition was completed indicated the title compound had been obtained in 33.9% non-isolated yield.

EXAMPLE 11

(R)-(+)-5-[[3,5-bis (1,1-dimethylethyl)-4-hydroxyphenyl]methyl]-4-thiazolidinone The title compound was prepared from 2.07 g (4.86 moles) of (3αS,5R)-5-[[3,5-(1,1-dimethylethyl)-4-hydroxyphenyl]methyl]-3-(1-phenylethyl)-4-thiazolidinone using 9.72 moles (2 equivalents) of calcium following the procedure of Example 1C. HPLC assay of the reaction solution after calcium addition was completed indicated the title compound had been obtained in 42.6% non-isolated yield.

EXAMPLE 12

5-[[3,5-bis (1,1-dimethylethyl)-4-hydroxyphenyl]methyl]- 4-thiazolidinone

A. 5-[[3,5-bis (1,1-dimethylethyl)-4-hydroxyphenyl]methyl]-3-diphenylmethyl-4-thiazolidinone 3-[3,5-bis(1,1-dimethylethyl)-4-hydroxyphenyl]-2-mercaptopropanoic acid (2.0 g; 6.45 moles), prepared substantially in accordance with the method described in Example 1A, was suspended in 20 ml of toluene. Under a nitrogen atmosphere, 0.2 g (6.45 mmoles) of paraformaldehyde was added, followed by 1.18 g (6.45 moles) of aminodiphenylmethane. An additional 10 ml of toluene was added and the resulting solution was heated at reflux temperature for 70 minutes with removal of water by means of a Dean-Stark apparatus. The solution was allowed to cool, after which the toluene was distilled off until about 10 ml of a light, brown solution remained. Fifteen milliliters of hexanes were added and the resultant solution was partitioned between ethyl acetate and 1N hydrochloric acid. The organic layer was washed with a saturated sodium bicarbonate solution and a brine solution, dried with sodium sulfate, filtered, and evaporated to provide a foam. The crude product was purified by silica gel chromatography and evaporated under vacuum to provide 2.99 g of a yellow foam. mp 286°–287° C. (dec).

Analysis Calculated for $C_{31}H_{37}NO_2S$: Theory: C, 76.35; H, 7.65; N, 2.87; Found: C, 76.46; H, 7.69; N, 2.77.

B. 5-[[3,5-bis(1,1-dimethylethyl)-4-hydroxyphenyl]methyl]-4-thiazolidinone

The title compound was prepared from 750 mg (1.54 mmoles) of the compound of Example 12A, substantially in accordance with the procedure described in Example 1C. Such reaction provided 0.66 g of title compound as a white solid.

EXAMPLE 13

5-[[3,5-bis(1,1-dimethylethyl)-4-hydroxyphenyl]methyl]- 4-thiazolidinone

A. 5-[[3,5-bis (1,1-dimethylethyl)-4-hydroxyphenyl]methyl-3-(4-carboxybenzyl)-4-thiazolidinone 3-[3,5-bis(1,1-dimethylethyl)-4-hydroxyphenyl]-2mercaptopropanoic acid (2.0 g; 6.45 mmoles), prepared substantially in accordance with the method described in Example 1A, was suspended in 20 ml of toluene. Under a nitrogen atmosphere, 0.2 g (6.45 mmoles) of paraformaldehyde and 0.98 g (6.45 mmoles) of 4-(aminomethyl)benzoic acid was added. An additional 20 ml of toluene was added and the mixture was heated at reflux temperature for 3 hours with removal of water by means of a Dean-Stark apparatus. The resultant mixture was then stirred at room temperature for 10 days. Ethyl acetate was added and the solution was washed with a $^{50}/_{50}$ 1N hydrochloric acid/water solution and a brine solution, dried with sodium sulfate and then evaporated to provide 3.1 g of the above-titled compound as a yellow foam.

B. 5-[[3,5-bis(1,1-dimethylethyl)-4-hydroxyphenyl]methyl]-3-(carbomethoxybenzyl)-4-thiazolidinone A portion of the foam prepared above (2.67 g; 5.87 mmoles) was dissolved in 54 ml of methanol to which was added 10 drops of concentrated sulfuric acid (approximately 0.07 ml) and the mixture was heated at reflux temperature, under nitrogen, for 30 minutes. An additional 10 drops of concentrated sulfuric acid was added and reflux was continued for an additional 5.5 hours. The mixture was then cooled to room temperature and stirred overnight. The next morning the mixture was heated, once again, to reflux and stirred at that temperature for an additional two hours. The mixture was then cooled to room temperature and partitioned between 300 ml of ethyl acetate and 100 ml of a 50% saturated sodium chloride solution. The organic layer was washed with brine solution, dried with sodium sulfate and then concentrated to provide 3.2 g of a viscous yellow oil. This oil was purified by silica gel chromatography using 1:2 ethyl acetate/hexanes, then 1:1 ethyl acetate/hexanes as eluent, to provide 2.2 g (80% yield) of the above titled compound as a white foam.

Analysis Calculated for $C_{27}H_{35}NO_4S$: Theory: C, 69.05; H, 7.51; N, 2.98; Found: C, 68.68; H, 7.80; N, 2.97.

C. 5-[[3,5-bis(1,1-dimethylethyl)-4 -hydroxyphenyl]methyl]-4-thiazolidinone

The title compound was prepared from 600 mg (1.28 mmoles) of the compound of Example 13B, substantially in accordance with the procedure described in Example 1C. Such reaction provided 0.54 g of title compound as a yellow solid.

EXAMPLE 14

5-[[3,5-bis(1,1-dimethylethyl)-4-hydroxyphenyl]methyl--4-thiazolidinone

A. 5-[[3,5-bis (1,1-dimethylethyl)-4-hydroxyphenyl]methyl]-3-benzyl-4-thiazolidinone 3-[3,5-bis-(1,1-dimethylethyl)-4-hydroxyphenyl]-2-mercaptopropanoic acid (4.58 g; 14.75 mmole), prepared substantially in accordance with the method described in Example 1A, was suspended in 50 ml of toluene. Under a nitrogen atmosphere, 0.45 g (15.0 mmoles) of paraformaldehyde was added followed by 1.67 grams (15.56 mmoles) of benzylamine. The resulting solution was heated at reflux temperature for one hour with removal of water by means of a Dean-Stark apparatus. The solution was allowed to cool to room temperature. Fifty milliliters of ethyl acetate was added and the resultant clear, yellow solution was extracted with 35 ml of a 0.5N hydrochloric acid solution, resulting in a cloudy yellow organic layer. An additional 30 ml of ethyl acetate was added to the cloudy organic layer and the resulting solution was extracted again with 35 ml of a 0.5N hydrochloric acid solution, resulting in yet another cloudy organic layer. Fifteen milliliters of ethyl acetate was added to the cloudy organic layer which was then washed with 30 ml of a 1:1 bicarbonate/brine solution, followed by 30 ml of a brine solution. The resulting solution was then dried with sodium sulfate, filtered and evaporated to provide 7.2 g of a viscous, cloudy oil.

Fifty milliliters of hexanes were added to dissolve the oil, and the resulting solution was heated to reflux and then cooled slowly to room temperature to provide a white slurry. After one hour the slurry was filtered, the recovered solids were washed with two 5 ml portions of hexanes and then dried in a vacuum oven to provide 5.34 g of a pale, yellow solid. mp 125°–127° C.

Analysis Calculated for $C_{25}H_{33}NO_2S$: Theory: C, 72.95; H, 8.08; N, 3.40; Found: C, 72.35; H, 8.13; N, 3.49; MS=411.

B. 5-[[3,5-bis (1,1-dimethylethyl)-4-hydroxyphenyl]methyl-4-thiazolidinone

The title compound was prepared from 1.55 g (3.77 moles) of the compound of Example 14A, substantially in accordance with the procedure described in Example 1C. Such reaction provided 0.71 g of a white solid (59% yield).

EXAMPLE 15

(R)-(+)-5-[[3,5-his (1,1-dimethylethyl)-4-hydroxyphenyl]methyl]-4-thiazolidinone Title product was prepared substantially in accordance with the procedure described in Example 1C using 5 ml of sieve-dried toluene as a co-solvent in place of tetrahydrofuran. After the reaction was quenched with ammonium chloride, 20 ml of water and 10 ml of toluene were added and the mixture was partitioned. The aqueous layer was extracted twice with 10 ml of toluene. The toluene layers were combined, washed with 10 ml of brine and then dried over sodium sulfate. The resulting dried solution was evaporated to yield 135 mg of a viscous, cloudy oil. Hexanes (10 ml) were added to the oil and the mixture was heated to reflux temperature. The mixture was allowed to cool and was stirred for one hour at room temperature. The resulting white precipitate was recovered and dried in a vacuum oven, to yield 32 mg of title product.

EXAMPLE 16

(3αR,5R)-5-[[3,5-bis(1,1-dimethylethyl)-4-hydroxyphenyl]methyl]-3-(1-phenylethyl)-4-thiazolidinone The hexanes crystallization filtrate from example 1B was heated to 30°–40° C. with stirring to induce crystallization of the more soluble diastereomer. After the crystallization was initiated, the mixture was allowed to stand overnight. The solvent was decanted and the crystals were rinsed with hexanes and dried to afford 54.6 g (27% yield) of subtitled compound as a white solid. HPLC analysis indicated a 98.5:1.5 ratio of diastereomers. mp 110°–111° C.

[a]589=+151.08 (c=1, $CHCl_3$)

Analysis Calculated for $C_{26}H_{35}NO_2S$: Theory: C, 73.37; H, 8.29; N, 3.29. Found: C, 73.49; H, 8.37; N, 3.33.

EXAMPLE 17

(3αS, 5S)-5-[[3,5-bis (1,1-dimethylethyl)-4-hydroxyphenyl]methyl]-3-(1-phenylethyl)-4-thiazolidinone The hexanes crystallization filtrate from example 2A was allowed to stand at room temperature for 32 h as crystallization of the more soluble diastereomer as long needles occurred. The solvent was decanted and the crystals were rinsed with hexanes and dried to afford 3.1 g (7% yield) of subtitled compound as a white solid. mp 111°–112° C.

[a]589=−153.49 (c=1, $CHCl_3$)

Analysis Calculated for $C_{26}H_{35}NO_2S$: Theory: C, 73.37; H, 8.29; N, 3.29. Found: C, 73.54; H, 8.33; N, 3.39.

As noted above, the present invention provides a method of treating inflammatory bowel disease in mammals. Such activity was demonstrated in the following test system.

Male Sprague-Dawley rats from Charles River Laboratories, Portage, Mich. (weight approximately 250 g) were dosed orally with test compound (30 mg/kg) or vehicle (control). Two hours after dosing, each animal received 2 ml of a 2.5% acetic acid intracolonic enema via a cannula, the tip of which was placed 8 cm above the anal verge. This concentration of acetic acid produced a severe inflammatory response in the colon characterized by rectal bleeding, diarrhea, epithelial erosions and destructions of crypts and gland cells. Six hours from the enema the test animals were then given a second dose of test compound or vehicle. Twenty four hours later the test and control animals were killed and the distal ten centimeters of the colon were removed and opened longitudinally. The tissue lesions contained within the removed, opened, section of colon were scored by three independent blinded observers on a scale of 0 to 4 (zero=normal, four=worst inflammation). In each test group 5–7 rats were used. Test results from animals given test compound dissolved in vehicle were compared with test results from animals given vehicle alone in order to determine the percentage of lesion inhibition attributable to the test compound. The results of such testing are reported in Table I below:

TABLE I

Inhibition of Acetic Acid Induced Colitis

| Compound | % Inhibition |
| --- | --- |
| 3-[3,5-bis(1,1-dimethylethyl)-4-hydroxyphenyl]-2-mercaptopropanoic acid | 18 |
| (3αR,5S)-5-[[3,5-bis(1,1-dimethylethyl)-4-hydroxyphenyl]methyl]-3-(1-phenylethyl)- | 36 |

TABLE I-continued

Inhibition of Acetic Acid Induced Colitis

| Compound | % Inhibition |
|---|---|
| 4-thiazolidinone | |
| (3αR,5R)-[[3,5-bis(1,1-dimethylethyl)-4-hydroxyphenyl]methyl]-3-(1-phenylethyl)-4-thiazolidinone | 30 |
| 5-[[3,5-bis(1,1-dimethylethyl)-4-hydroxyphenyl]methyl]-3-(carbomethoxybenzyl)-4-thiazolidinone | 11 |

The data in Table 1 establish that the compounds used in the method of present invention can be used to treat inflammatory bowel disease. The term "inflammatory bowel disease", as used for purposes of the present invention, means any disorder of the digestive system which is characterized by inflammation. Examples of such disorders include Crohn's disease, mucous coliris, ulcerative coliris, psuedomembranous enterocolitis, non-specific colonic ulcers, collagenous colitis, cathartic colon, ulcerative proctitis, radiation enteriris and colitis, idiopathic diffuse ulcerative nongranulamatus enteritis, nonsteroidal antiinflammatory drug induced inflammations, celic sprue and the like.

The method of the present invention comprises administering to a mammal suffering from inflammatory bowel disease an effective amount of one or more of the compounds of Formula II or III. Administration may be done either therapeutically or prophylactically and is accomplished by means of pharmaceutical compositions which are prepared by techniques well known in the pharmaceutical sciences.

The compounds of Formulae II and III are effective over a wide dosage range in treating inflammatory bowel disease. Thus, as used herein, the term "effective amount" refers to a dosage range of from about 0.001 to about 200 mg/kg of body weight per day. In the treatment of adult humans, the range of about 0.1 to about 50 mg/kg, in single or divided doses, is preferred. However, it will be understood that the amount of compound actually administered will be determined by a physician in light of the relevant circumstances, including the condition to be treated, the choice of compound to be administered, the chosen route of administration, the age, weight, and response of the individual patient, and the severity of the patient's symptoms. Therefore, the above dosage ranges are not intended to limit the scope of the invention in any way.

While the compounds of Formulae II and III are preferably administered orally or intrarectally, the compounds may also be administered by a variety of other routes such as the transdermal, subcutaneous, intranasal, intramuscular and intravenous routes.

The present invention provides new compounds of Formulae II and III. Accordingly, the present invention is also directed to pharmaceutical compositions which include at least one compound of Formulae II or III in association with one or more pharmaceutically acceptable diluents, excipients or carriers therefor.

In making the pharmaceutical compositions of the present invention, one or more compounds of Formulae II or III will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The following formulation examples may employ as active ingredients any of the compounds of Formula II or III. The examples are illustrative only and are not intended to limit the scope of the invention in any way.

EXAMPLE 18

Hard gelatin capsules are prepared using the following ingredients:

| | Quantity (mg/capsule) |
|---|---|
| 3-[3,5-bis(1,1-dimethylethyl)-4-hydroxyphenyl]-2-mercaptopropanoic acid | 250 |
| Starch, dried | 200 |
| Magnesium stearate | 10 |

The above ingredients are mixed and filled into hard gelatin capsules in 460 mg quantities.

EXAMPLE 19

A tablet formula is prepared using the ingredients below:

| | Quantity (mg/tablet) |
|---|---|
| 3-[3,5-bis(1,1-dimethylethyl)-4-hydroxyphenyl]-2-mercaptopropanoic acid | 250 |
| Cellulose, microcrystalline | 400 |
| Silicon dioxide, fumed | 10 |
| Stearic Acid | 5 |

The components are blended and compressed to form tablets each weighing 665 mg.

EXAMPLE 20

An aerosol solution is prepared containing the following components:

|  | Weight % |
|---|---|
| 3-[3,5-bis(1,1-dimethylethyl)-4-hydroxyphenyl]-2-mercaptopropanoic acid | 250.00 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 21

Tablets each containing 60 mg of active ingredient are made up as follows:

|  | Quantity (mg/tablet) |
|---|---|
| (3αR,5S)-5-[[3,5-bis(1,1-dimethylethyl)-4-hydroxyphenyl]methyl]-3-(1-phenylethyl)-4-thiazolidinone | 60.0 mg |
| Starch | 45.0 mg |
| Microcrystalline Cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150.0 mg |

The active ingredient, starch and cellulose are passed through a No. 45 U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. Sieve, are then added to the granules which, after mixing, are compressed by a tablet machine to yield tablets each weighing 150 mg.

EXAMPLE 22

Capsules each containing 80 mg of medicament are made as follows:

|  | Quantity (mg/capsule) |
|---|---|
| (3αR,5S)-5-[[3,5-bis(1,1-dimethylethyl)-4-hydroxyphenyl]methyl]-3-(1-phenylethyl)-4-thiazolidinone | 80 mg |
| Starch | 59 mg |
| Microcrystalline Cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 23

Suppositories each containing 225 mg of active ingredient are made as follows:

|  | Quantity (mg/suppository) |
|---|---|
| (3αR,5S)-5-[[3,5-bis(1,1-dimethylethyl)-4-hydroxyphenyl]methyl]-3-(1-phenylethyl)-4-thiazolidinone | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold off nominal 2 g capacity and allowed to cool.

EXAMPLE 24

Suspensions each containing 50 mg of medicament per ml dose are made as follows:

|  | Quantity |
|---|---|
| (3αR,5R)-5-[[3,5-bis(1,1-dimethylethyl)-4-hydroxyphenyl]methyl]-3-(1-phenylethyl)-4-thiazolidinone | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5.0 ml |

The medicament is passed through a No. 45 mesh U.S., sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 25

Capsules each containing 150 mg of medicament are made as follows:

|  | Quantity (mg/capsule) |
|---|---|
| (3αR,5R)-[[3,5-bis(1,1-dimethylethyl)-4-hydroxyphenyl]methyl]-3-(1-phenylethyl)-4-thiazolidinone | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A process for preparing a compound of the Formula I

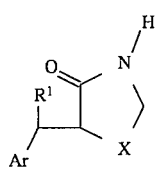

(I)

wherein:

Ar is (i) phenyl, (ii) phenyl substituted with from one to three substituents independently selected from $C_1$–$C_8$ alkyl, $C_2$–$C_6$ alkenyl, $C_2$–$C_6$ alkynyl, $C_1$–$C_8$ alkoxy, $C_1$–$C_8$ alkylthio, trifluoromethyl, $C_1$–$C_4$ alkylphenyl, phenyl, F, Cl, hydroxy, phenoxy, $C_1$–$C_4$ alkyloxyphenyl, thiophenyl, $C_1$–$C_4$ alkylthiophenyl, —N($R^6$)$_2$ or —N($R^6$)SO$_2R^6$, where each $R^6$ is independently hydrogen or $C_1$–$C_6$ alkyl or (iii) 1- or 2-napthyl;

$R^1$ is $C_1$–$C_6$ alkyl, $C_1$–$C_4$ alkylphenyl, hydrogen, phenyl or phenyl substituted with one or two substituents independently selected from Cl, F, $C_1$–$C_4$ alkyl, $C_1$–$C_4$ alkoxy, trifluoromethyl, NH$_2$, —NH($C_1$–$C_4$ alkyl), —N($C_1$–$C_4$ alkyl)$_2$ or $C_1$–$C_4$ alkylthio; and X is S=(O)$_m$ where m is 0, 1 or 2, comprising reducing a hiazolidinone of the Formula II.

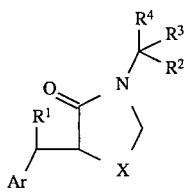

(II)

wherein:

Ar, $R^1$, and X are as defined above; and $R^2$ and $R^3$ are each independently hydrogen, $C_1C_6$ alkyl, phenyl, phenyl substituted with from one to three substituents independently selected from $C_1C_6$ alkyl, or —CO$_2R^5$, where $R^5$ is hydrogen or $C_1$–$C_6$ alkyl; and $R^4$ is phenyl or phenyl substituted with from one to three substituents independently selected from $C_1C_6$ alkyl, or —CO$_2R^5$, where $R^5$ is hydrogen or $C_1$–$C_6$ alkyl;

with approximately two moles of an alkali or approximately one mole of an alkali-earth metal for every mole of thiazolidinone substrate in the presence of ammonia or an amine of the formula H$_2$N$R^7$ where $R^7$ is $C_1$–$C_6$ alkyl.

2. A process of claim 1 which employs a thiazolidinone of the Formula II wherein Ar is phenyl substituted with from one to three substituents independently selected from $C_1$–$C_8$ alkyl, $C_1$–$C_8$ alkoxy, $C_1$–$C_4$ alkylphenyl, phenyl, F, Cl, hydroxy, phenoxy, $C_1$–$C_4$ alkylthiophenyl, or —N($R^6$)SO$_2R^6$ where each $R^6$ is independently hydrogen or $C_1$–$C_6$ alkyl.

3. A process of claim 2 which employs a thiazolidinone of the Formula II wherein Ar is phenyl substituted with from one to three substituents independently selected from $C_1$–$C_4$ alkyl, $C_1$–$C_6$ alkoxy or hydroxy.

4. A process of claim 3 which employs a thiazolidinone of the Formula II wherein Ar is phenyl substituted with hydroxy at the 4-position and a $C_1$–$C_4$ alkyl group at the 3-and 5-positions.

5. A process of claim 1 which employs a thiazolidinone of the Formula II wherein X is S=(O)$_m$ where m is 0.

6. A process of claim 3 which employs a thiazolidinone of the Formula II wherein X is S=(O)$_m$ where m is 0.

7. A process of claim 4 which employs a thiazolidinone of the Formula II wherein X is S=(O)$_m$ where m is 0.

8. A process of claim 1 which employs a thiazolidinone of the Formula II wherein $R^1$ is hydrogen.

9. A process of claim 4 which employs a thiazolidinone of the Formula II wherein $R^1$ is hydrogen.

10. A process of claim 7 which employs a thiazolidinone of the Formula II wherein $R^1$ is hydrogen.

11. A process of claim 1 which employs a thiazolidinone of the Formula II wherein $R^2$ and $R^3$ are each independently hydrogen, $C_1$–$C_4$ alkyl, phenyl or phenyl substituted with —CO$_2$($C_1$–$C_4$ alkyl); and $R^4$ is phenyl or phenyl substituted with —CO$_2$($C_1$–$C_4$ alkyl).

12. A process of claim 3 which employs a thiazolidinone of the Formula II wherein $R^2$ and $R^3$ are each independently hydrogen, $C_1$–$C_4$ alkyl, phenyl or phenyl substituted with —CO$_2$($C_1$–$C_4$ alkyl); and $R^4$ is phenyl or phenyl substituted with —CO$_2$($C_1$–$C_4$ alkyl).

13. A process of claim 4 which employs a thiazolidinone of the Formula II wherein $R^2$ and $R^3$ are each independently hydrogen, $C_1$–$C_4$ alkyl, phenyl or phenyl substituted with —CO$_2$($C_1$–$C_4$ alkyl) and $R^4$ is phenyl or phenyl substituted with —CO$_2$($C_1$–$C_4$ alkyl).

14. A process of claim 6 which employs a thiazolidinone of the Formula II wherein $R^2$ and $R^3$ are each independently hydrogen, $C_1$–$C_4$ alkyl, phenyl or phenyl substituted with —CO$_2$($C_1$–$C_4$ alkyl) and $R^4$ is phenyl or phenyl substituted with —CO$_2$($C_1$–$C_4$ alkyl).

15. A process claim 7 which employs a thiazolidinone of the Formula II wherein $R^2$ and $R^3$ are each independently hydrogen, $C_1$–$C_4$ alkyl, phenyl or phenyl substituted with —CO$_2$($C_1$–$C_4$ alkyl) and $R^4$ is phenyl or phenyl substituted with —CO$_2$($C_1$–$C_4$ alkyl).

16. A process of claim 10 which employs a thiazolidinone of the Formula II wherein $R^2$ and $R^3$ are each independently hydrogen, $C_1$–$C_4$ alkyl, phenyl or phenyl substituted with —CO$_2$ ($C_1$–$C_4$ alkyl) and $R^4$ is phenyl or phenyl substituted with —CO$_2$ ($C_1$–$C_4$ alkyl).

17. A process of claim 16 in which the final product is (R)-(+)-5-[[3,5-bis (1,1-dimethylethyl)-4-hydroxyphenyl]methyl]-4-thiazolidinone.

18. A process of claim 16 in which the final product is (S)-(–)-5-[[3,5-bis (1,1-dimethylethyl)-4-hydroxyphenyl]methyl]-4-thiazolidinone.

19. A process of claim 1 in which the alkali or alkali-earth metal employed is sodium, calcium, lithium, potassium or magnesium.

20. A process of claim 4 in which the alkali or alkali-earth metal employed is sodium, calcium, lithium, potassium or magnesium.

21. A process of claim 7 in which the alkali or alkali-earth metal employed is sodium, calcium, lithium, potassium or magnesium.

22. A process of claim 10 in which the alkali or alkali-earth metal employed is sodium, calcium, lithium, potassium or magnesium.

23. A process of claim 16 in which the alkali or alkali-earth metal employed is sodium, calcium, lithium, potassium or magnesium.

24. A process of claim 23 in which the metal employed is lithium.

25. A process of claim 1 which employs ammonia.
26. A process of claim 4 which employs ammonia.
27. A process of claim 7 which employs ammonia.
28. A process of claim 10 which employs ammonia.
29. A process of claim 16 which employs ammonia.
30. A process of claim 23 which employs ammonia.
31. A process of claim 24 which employs ammonia.
32. A process of claim 31 which prepares (R)-(+)-5-[3,5-bis(1,1-dimethylethyl)-4-hydroxyphenyl]methyl]-4-thiazolidinone.

33. A process of claim 31 which prepares (S)-(–)-5-[3,5-bis(1,1-dimethylethyl)-4-hydroxyphenyl]methyl]-4-thiazolidinone.

* * * * *